United States Patent [19]
Jarin

[11] Patent Number: 5,149,074
[45] Date of Patent: Sep. 22, 1992

[54] PATIENT SUPPORT HAVING A LONG RANGE OF VERTICAL DISPLACEMENT

[75] Inventor: Jean-Pierre Jarin, Lamorlaye, France

[73] Assignee: General Electric CGR SA, Issy les Moulineaux, France

[21] Appl. No.: 683,492

[22] Filed: Apr. 10, 1991

Related U.S. Application Data

[63] Continuation of Ser. No. 486,413, Feb. 28, 1990, abandoned.

[30] Foreign Application Priority Data

Mar. 23, 1989 [FR] France ................ 89 03846

[51] Int. Cl.$^5$ ............................................. A61G 13/00
[52] U.S. Cl. ................................................ 5/601; 5/610
[58] Field of Search ............ 414/589; 901/15, 23; 378/208, 209, 91, 196, 179; 269/322-326; 254/124; 108/145; 187/17, 18; 5/11, 63

[56] References Cited

U.S. PATENT DOCUMENTS

| | | |
|---|---|---|
| 2,884,144 | 4/1959 | Laws ................... 414/589 |
| 3,818,516 | 6/1974 | Hopper et al. . |
| 3,965,573 | 6/1976 | Mims ................... 269/322 |
| 4,283,764 | 8/1981 | Crum et al. ........... 901/15 |
| 4,657,235 | 4/1987 | Schar .................. 269/322 |
| 4,692,087 | 9/1987 | Olsen .................. 414/589 |
| 4,795,142 | 1/1989 | Schoefer ............... 269/322 |
| 4,842,259 | 6/1989 | Rice ................... 269/323 |

FOREIGN PATENT DOCUMENTS

| | | |
|---|---|---|
| 58734 | 1/1982 | European Pat. Off. .......... 414/589 |
| 0220501 | 5/1987 | European Pat. Off. . |
| 2201921 | 7/1973 | Fed. Rep. of Germany . |
| 891094 | 12/1981 | U.S.S.R. ................... 269/322 |

Primary Examiner—Robert C. Watson
Attorney, Agent, or Firm—Oblon, Spivak, McClelland, Maier & Neustadt

[57] ABSTRACT

The vertical displacement of a patient support table for a radiology apparatus is obtained by means of an electromechanical device constituted by arms which are connected to each other and to the support table by means of powered articulations with synchronized movements of rotation. A relatively small minimum height of the order of 60 centimeters is thus obtained.

5 Claims, 3 Drawing Sheets

PATIENT SUPPORT HAVING A LONG RANGE OF VERTICAL DISPLACEMENT

This application is a Continuation of application Ser. No. 07/486,413, filed on Feb. 28, 1990, now abandoned.

BACKGROUND OF THE INVENTION

1. Field of the Invention

This invention relates to patient supports and more particularly to those employed in radiology devices.

2. Description of the Prior Art

A radiology device comprises an x-ray source and an x-radiation detector which is displaced in coordinate paths in order to obtain x-ray images of a patient who is usually recumbent on a support. By way of example, this support consists of a pedestal surmounted by a table on which the patient lies. The pedestal and the table are equipped with electromechanical devices for displacing the table along two axes located in a horizontal plane and a third axis which is vertical. In addition, the pedestal itself is capable of moving on rails in some instances.

For reasons of convenience of examination of the patient by the practitioner and ease of transfer of the source or of the detector beneath the table, the maximum height is approximately 120 centimeters above the ground. Moreover, the minimum height which is established by design is approximately one meter. This minimum height does not facilitate loading or unloading of the patient on or from the table since caster beds are lower in height.

In order to solve this problem, it clearly appears to be sufficient to modify existing mechanical devices with a view to obtaining a smaller minimum height of 60 centimeters, for example. This solution is not possible since the mechanisms usually employed on tables are not of the retractable or folding type.

The object of the present invention is therefore to construct a patient support having a long range of vertical displacement so as to obtain a relatively small minimum height, thus facilitating loading or unloading of the patient.

SUMMARY OF THE INVENTION

The invention relates to a patient support which essentially comprises a table, one end of which is in an overhung position whilst the other end is attached to a first articulation having a horizontal axis of rotation, a first arm to which said first articulation is attached at one end whilst the other end is provided with a second articulation having a horizontal axis of rotation, a second arm to which said second articulation is attached at one end whilst the other end is provided with a third articulation having a horizontal axis of rotation, and a pedestal which is rigidly fixed to the ground and on which the third articulation is fixed, said articulations being motor-driven and equipped with servomechanisms controlled by a microprocessor so as to ensure that the displacement of the arms produces a vertical displacement of the table whilst this latter remains parallel to the horizontal plane.

DETAILED DESCRIPTION OF THE INVENTION

The patient support in accordance with the invention comprises a horizontal table 10 which is maintained in an overhung position at one end 11 on a first articulation 12.

Figure 2:
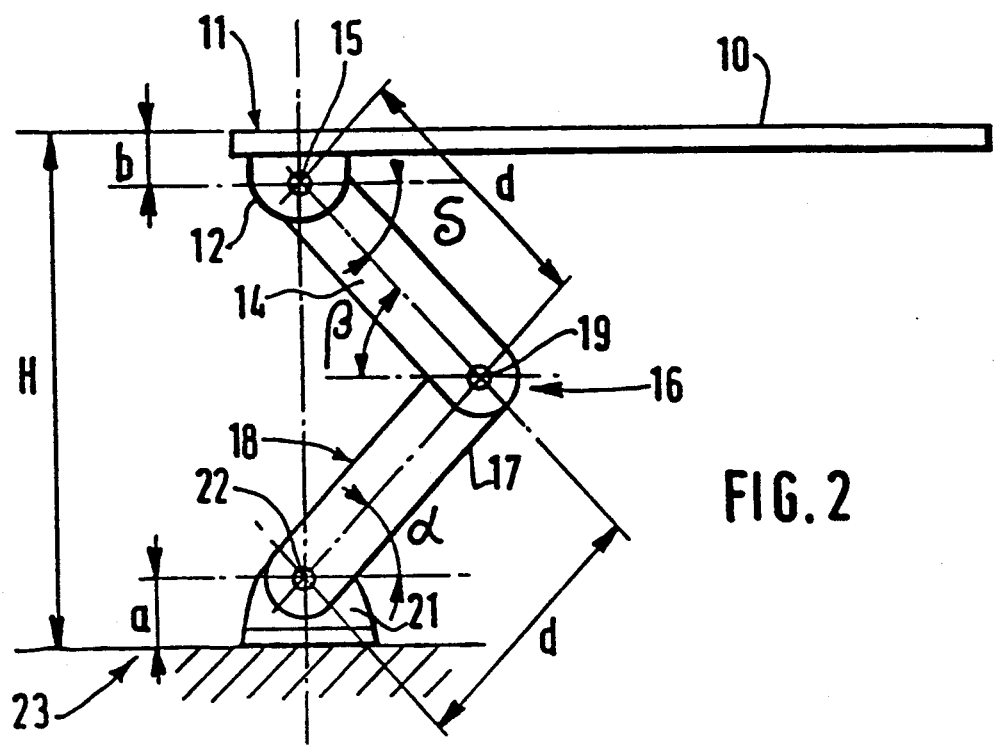
FIG. 2 is a diagram which serves to define the relations to be complied with in order to displace the support, the table being intended to remain horizontal during the movement of extension of the patient support.

Said articulation 12 is attached to one end of a first arm 14 and enables the table 10 to rotate about a horizontal axis 15 (angle $\delta$- FIG. 2) which is parallel to the plane of the table 10 and perpendicular to the plane of FIG. 2. The other end of the arm 14 is connected by means of a second articulation 16 to one end 17 of a second arm 18. Said articulation which is attached to the arm 18 enables the arm 14 to rotate about a horizontal axis 19 parallel to the axis 15 (angle $\beta$- FIG. 2). Finally, the other end of the arm 18 is supported by a third articulation 21 on a pedestal 23 which is rigidly fixed to the ground 29 and said third articulation enables the arm 18 to rotate about a horizontal axis 22 (angle $\alpha$- FIG. 2) which is parallel to the axes 15 and 19.

The articulations 12, 16 and 21 can be motor-driven on each of the axes and each equipped with a servomechanism controlled by a microprocessor (not shown in the drawings). In an alternative embodiment, only one articulation is motor-driven and the angular movements of the other two articulations are synchronized mechanically with the first. In both cases, the angular movements of the articulations must be such that the movement of extension or of folding-back of the arms complies with two relations as follows:

$$\alpha = \beta = \delta$$

$$H = a + b + 2 d \sin \alpha$$

H being the height of the table with respect to the level of the ground 29, a being the height of the axis 22 with respect to the ground, b being the distance between the axis 15 and the top of the table 10, d being the length of the arms 14 and 18.

The first relation corresponds to synchronized pivotal movements of the arms and of the table.

In order to conceal the system of arms and articulations, the table 10 is provided directly above the arms and articulations with a skirt 24 in three sections which fit one inside the other at the time of folding-back.

Figure 3:
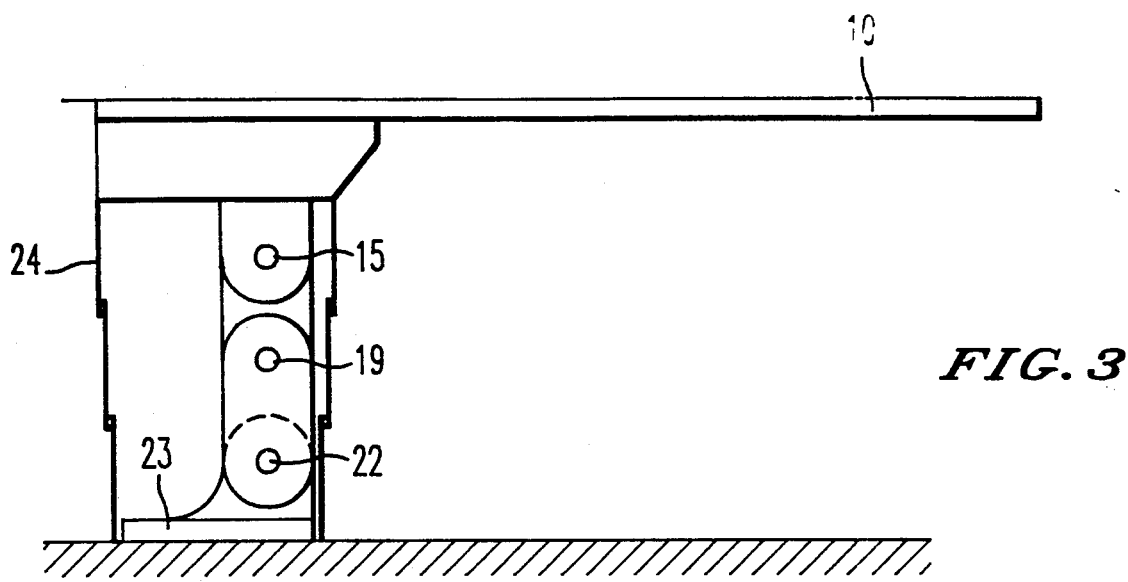
FIG. 3 is a side view of the patient support which is in the fully extended state in the vertical direction.

When the patient support is fully extended (FIG. 3), the angles $\alpha$, $\beta$ and $\delta$ are equal to 90° and the three axes 15, 19 and 22 are aligned in the same vertical plane perpendicular to the plane of FIG. 3. Moreover, the three sections of the skirt 24 are also extended.

Figure 4:
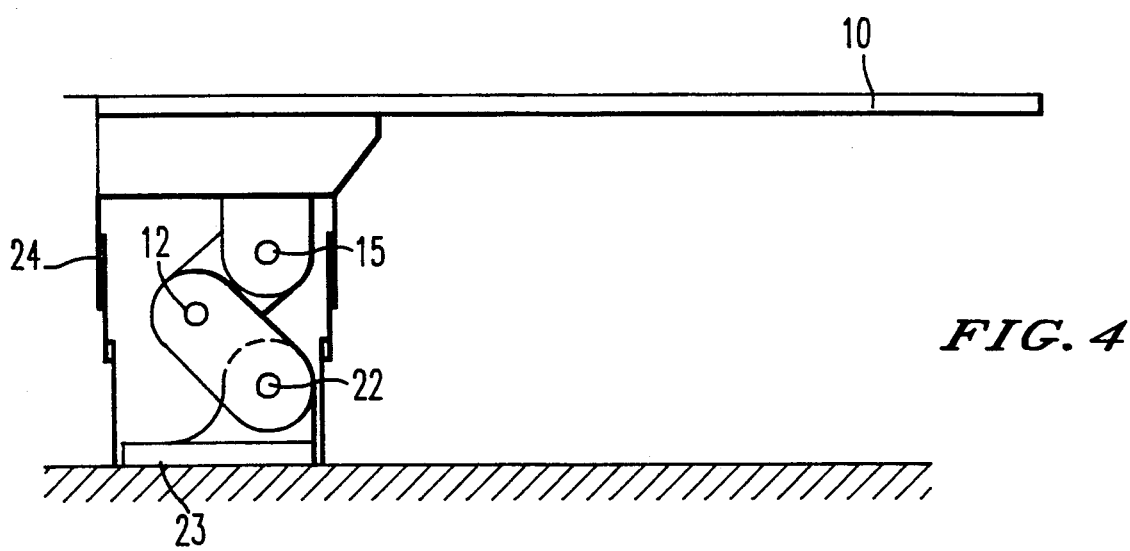
FIG. 4 is a side view of the patient support in the case of intermediate extension.

FIG. 4 shows an intermediate position in height of the patient support corresponding for example to $\alpha=\beta=\delta=45°$. It will be noted that the movement of the arms takes place in the direction opposite to that which is contemplated in FIG. 2 in the event of folding-back. The skirt sections overlap each other to a partial extent.

Figure 5:
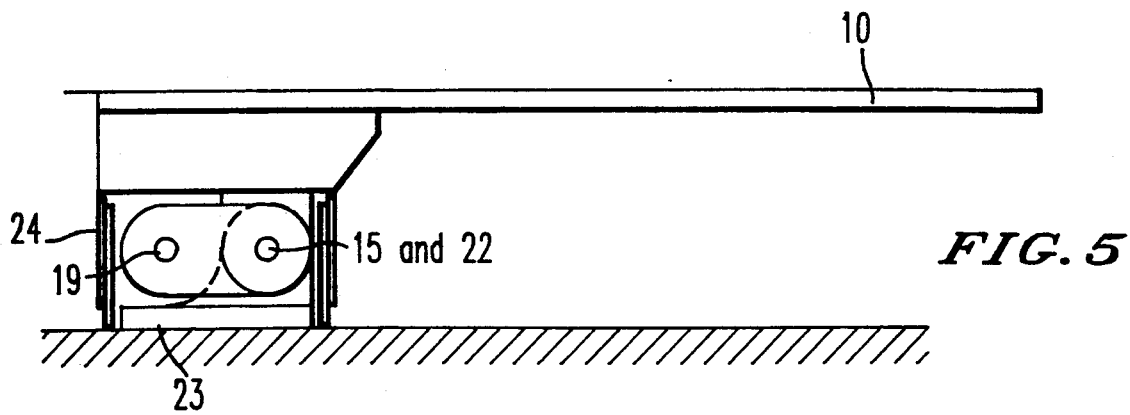
FIG. 5 is a side view of the patient support in the case of minimum extension.

FIG. 5 shows the completely folded-back position, the two arms 14 and 18 being parallel to each other and to the horizontal plane and the three axes 15, 19 and 22 being in the same horizontal plane. The skirt sections overlap completely.

Figure 1:
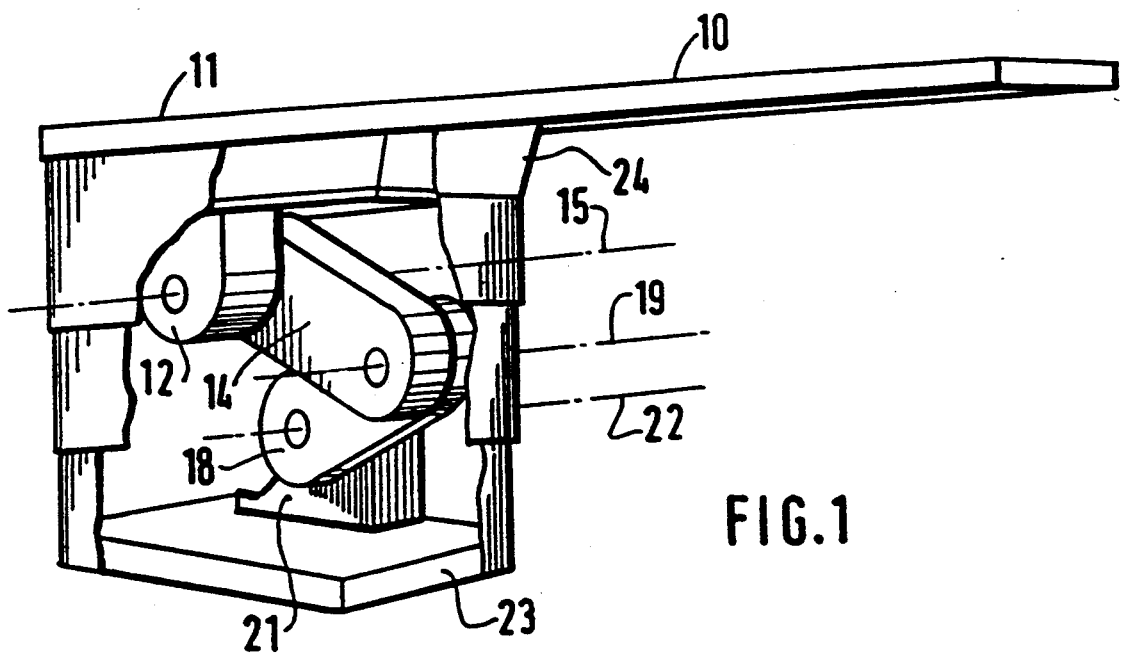
FIG. 1 is a cutaway view in perspective showing the patient support in accordance with one embodiment of the present invention.

In order to ensure that the arms 14 and 18 and the articulations 12, 16 and 22 can be folded-back against each other, they must be placed in different and parallel vertical planes as shown in the perspective view of FIG. 1.

The invention has been described with a device comprising two arms and three articulations but remains applicable to a larger or smaller number of arms and articulations.

Figure 6:
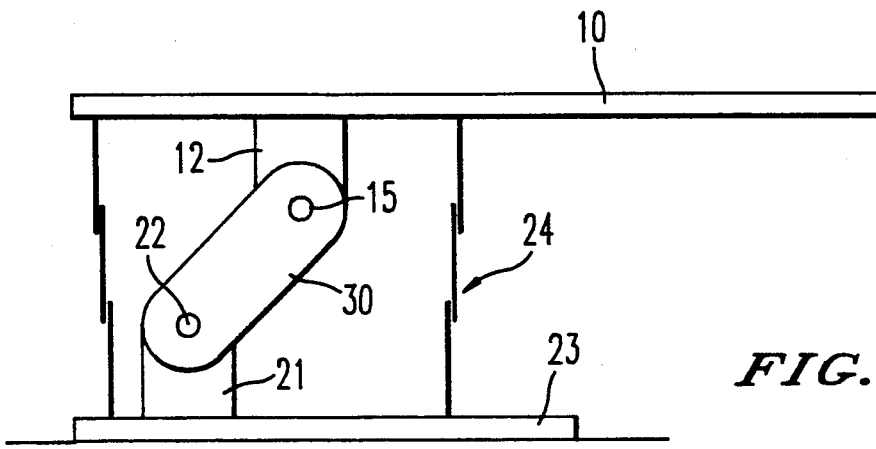
FIG. 6 is a side view of the patient support in accordance with a further embodiment of the present invention.

FIG. 6 shows a patient support according to the invention which comprises only one arm 30 corresponding to the lower arm 18 of the embodiment of FIG. 2 and two articulations 12 and 21 corresponding to the same of FIG. 2.

Figure 7:
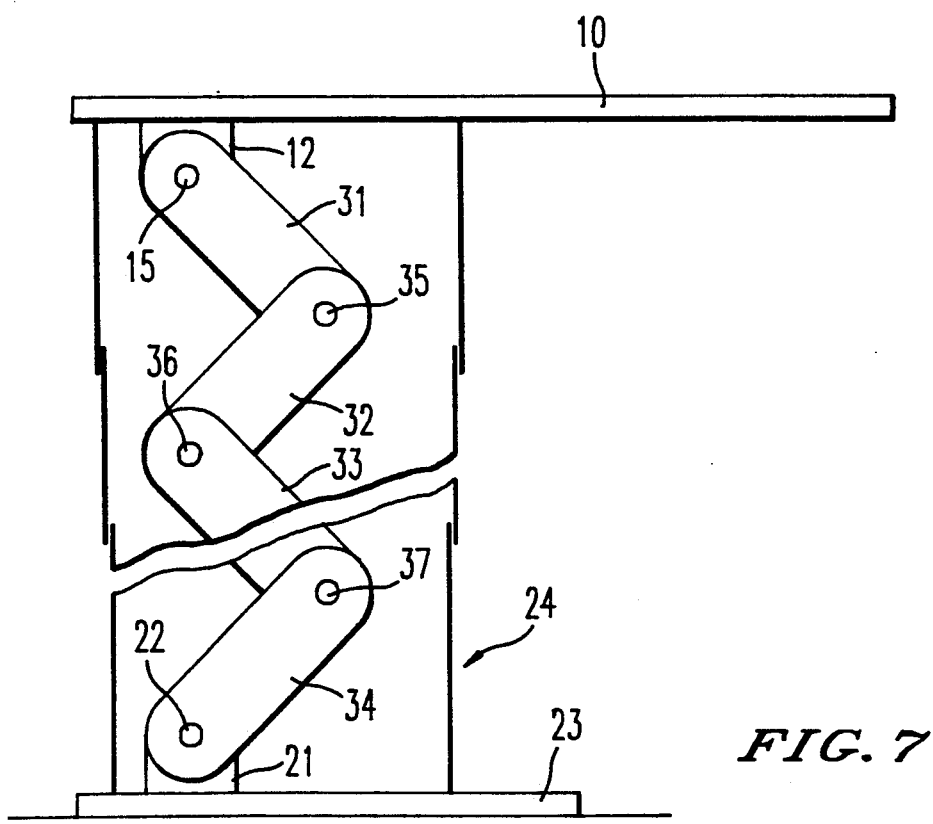
FIG. 7 is a side view of the patient support in accordance with yet another embodiment of the present invention.

FIG. 7 shows a patient support according to the invention which comprises more than two arms and three articulations. As can be seen from this Figure, there are four arms 31, 32, 33, 34 and five articulations 12, 21, 35 and 37 in this embodiment.

Moreover, the means for obtaining the angular movements of the articulations and their synchronization have not been described in detail since they are within the capacity of those versed in the art and do not constitute an inventive step.

I claim:

1. A patient support, wherein said support comprises a table, having a surface, one end of which is in an overhung position whilst the other end is attached to an articulation having a horizontal axis of rotation, at least one arm to which said articulation is attached whilst the other end of the at least one arm is attached to another articulation having a horizontal axis of rotation, and a pedestal which is rigidly fixed to the ground and on which said another articulation is fixed, wherein said articulations are provided with means for actuating them in angular movements such that the pivotal displacement f the at least one arm and of the table are synchronized so that an acute angle formed between the at least one arm at an associated articulation and a horizontal plane passing through the associated articulation is equal for each articulation and wherein each of said articulations are situated in different and parallel vertical planes in order to be able to be folded-back against each other thereby providing that said horizontal axis of rotation of said articulation and said horizontal axis of rotation of said other articulation is in one and the same horizontal plane and that said at least one arm is also in said horizontal plane.

2. A patient support according to claim 1, wherein the means for actuating the articulations comprise at least one motor for driving at least one articulation and mechanical means for synchronizing the movement of the other articulate with the movement of the articulation which is equipped with the driving motor.

3. A patient support according to claim 1, wherein the means for actuating the articulations comprise one driving motor per articulation and means for synchronizing the movements of said motors.

4. A patient support according to claim 1, wherein the number of arms is two and wherein the number of articulations is three.

5. A patient support according to claim 1, wherein the number of arms is greater than two and wherein the number of articulations is greater than three.